(12) United States Patent
Dettling (10) Patent No.: US 6,360,113 B1
(45) Date of Patent: Mar. 19, 2002

(54) PHOTOPLETHYSMOGRAPHIC INSTRUMENT

(75) Inventor: Allen Dettling, Broomfield, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 09/465,858

(22) Filed: Dec. 17, 1999

(51) Int. Cl.[7] .............................................. A61B 5/00
(52) U.S. Cl. ...................................... 600/322; 600/336
(58) Field of Search .............................. 600/310, 322, 600/323, 330, 336

(56) References Cited

U.S. PATENT DOCUMENTS 4,819,752 A * 4/1989 Zelin ........................... 600/322
5,351,685 A * 10/1994 Potratz ........................ 600/330

* cited by examiner

*Primary Examiner*—Eric F. Winakur
(74) *Attorney, Agent, or Firm*—Marsh Fischmann & Breyfogle LLP (57) ABSTRACT

The pulse oximeter instrument of the present invention includes switched gain, channel rotation and bootstrap amplification features. In one embodiment, a time-division multiplexed gain circuit is provided in receiver circuitry and is equipped with a switched gain amplifier to faciliate the use of a fixed light source drive and otherwise improve the signal processing characteristics of the instrument. Signal processing is further enhanced via use of a transimpedance amplifier and bootstrap amplifier interconnected across one or more photodiodes. The apparatus time division multiplexes (TDM) the optical input channels to customize the gain response of the apparatus to the variable characteristics of each input channel. Thus, the channel-specific error sources are determined and precisely eliminated from the input data. The channels may also be rotated in subsequent signal conditioning that entails demultiplexing/multiplexing.

23 Claims, 7 Drawing Sheets

PHOTOPLETHYSMOGRAPHIC INSTRUMENT

FIELD OF THE INVENTION

This invention relates to medical monitoring instruments that use at least one light emitting device to illuminate a patient tissue site and is particularly applicable to photoplethysmographic arrangements having at least one detector that receives light from a plurality of light emitting devices and outputs a multiplexed signal in response thereto.

PROBLEM

It is a problem in the field of photoplethysmographic medical monitoring instruments to obtain light detector outputs of sufficient magnitude, quality, and stability to accurately measure the desired physiological characteristics of the subject. The light emitting devices that are used in probes have varying performance characteristics, the absorption characteristics of the tissue vary widely according to probe site and subject, and the presence of external influences such as ambient light can cause significant error components in the resultant measurements. These problems can be compounded in arrangements in which the detector receives light from a plurality of emitters and provides a multiplexed output signal in response thereto.

SOLUTION

The above-described problems are addressed and a technical advance achieved in the field by the photoplethysmographic instrument of the present invention.

In one aspect, the invention includes a plurality of light emitting devices, a light detector means for receiving light from the light emitting devices, and an amplifier means having a settable gain for amplifying a multiplexed detection signal indicative of the light received by the light detector means, wherein the amplitude of said multiplexed detection signal is maintainable within a predetermined amplitude range. Preferably, the multiplexed detection signal is a signal output by the detector means.

A monitoring means may be provided to monitor the amplitude of the multiplexed detection signal and to provide a digital control signal to set the gain of the amplifying means. In one approach, the multiplexed detection signal may be converted to a digital signal for processing by a digital processor, wherein an extracted amplitude value may be compared with a references value(s) defining said predetermined amplitude range. In the event the compared value is outside of the predetermined range, the digital processor may be preprogrammed to automatically provide a digital control signal to a switching means comprising the amplifier means, wherein an appropriate gain is applied via a transimpedance amplifier to maintain the detection signal within the predetermined range. By way of example, where the photoplethysmographic instrument is utilized with tissue thicknesses significantly greater/less than a predetermined norm, the applied gain may be automatically adjusted upward/downward by the monitoring means.

By virtue of utilizing an amplifying means with an adjustable gain to amplify a multiplexed detection signal fixed drive means may be advantageously employed to provide fixed drive signals for the light-emitting device(s). For example, different, fixed current signals may be applied to each different one of a plurality of laser diodes. The use of a fixed drive means serves to stabilize the output temperature versus wavelength characteristics of the light-emitting device(s), thereby reducing the potential for error associated with wavelength shift. Additionally, such an approach avoids the need for circuitry typically required to adjust the drive level of light emitting device(s).

Of particular note, in arrangements where a plurality of light sources are sequentially activated (e.g., by a time-division multiplexed (TDM) drive circuit) the gain applied by the amplifying means may be selectively set in corresponding relation to each of the successive portions of the resultant time-division multiplexed (TDM) detection signal. More particularly, in TDM applications, a control signal may be provided to effect the separate setting of a gain level to each sequential portion of the TDM detection signal. As will be appreciated, gain levels may be predetermined in relation to each of the light emitting devices based upon the known light intensity output attributes of the light emitting devices employed.

It should also be noted that in TDM applications, the plurality of light emitting devices may be activated so that each TDM detection signal portion includes a first subportion corresponding with activation of a corresponding one of the light emitting devices and a second subportion corresponding with a precedent or subsequent dark time during which all of the light emitting devices are inactive. In turn, the gain level applied to each given TDM detection signal portion may be applied to both of the first and second subportions thereof.

In additional aspects of the present invention, at least one light emitting device and a detector means (e.g. a photodiode detector) may be employed with an amplifying means that comprises bootstrap amplifier configuration or a balanced input transimpedance amplifier configuration. More particularly, in the bootstrap amplifier configuration, a first amplifier may be employed to maintain a substantially zero bias across the detector means and a second amplifier may be employed to present a substantially zero impedance load to the detector means. In this regard, a transimpedance amplifier and bootstrap amplifier may be interconnected across the detector means. Such an arrangement facilitates rapid gain switching in an amplifying means downstream of the detector means (e.g., in a switched gain circuit comprising the amplifying means as described above). Additionally, the noted bootstrap amplifier configuration may be employed with detector means to facilitate rapid gain switching in a drive means for one or more light emitter(s), wherein narrower drive pulses may be employed. Rapid gain switching is of particular merit in the above-noted TDM applications.

As indicated, a balanced input transimpedance amplifier configuration may also be employed in the amplifying means of the present invention. More particularly, first and second transimpedance amplifiers may be interconnected across a detector means, wherein a common gain level is applied to each of the amplifiers by corresponding first and second switched gain circuits. Again, the gain for each circuit may be set by a digital control signal.

In yet another aspect, an inventive apparatus is provided in a TDM arrangement that employs a signal rotating means. More particularly, the apparatus may comprise a plurality of light-emitting devices which are sequentially driven by a time-division multiplexing drive means and a light detector means for receiving a portion of the light that is transmitted by an illuminated patient site. The signal rotating means is provided to receive a detection signal indicative of the light received by the detection means, wherein the detection signal comprises a plurality of sequential portions corresponding with the sequential activation of the light emitters (e.g., the portions may be sequenced in the same order in which the light emitting devices are activated). The rotating means functions to change the order of the detection signal portions in accordance with a predetermined ordering scheme, and output a reordered signal. The signal rotating means may be advantageously employed to reduce switching noise occasioned by demultiplex/multiplex switching in a low pass filter.

In one embodiment comprising one or more of the above-noted aspects, an inventive apparatus uses a time-division multiplexed fixed drive to activate a plurality of emitters, and a detector with an amplifier having a time-division multiplexed input stage whose gain is digitally set to produce roughly uniform magnitude output signals for all of the input signals received as a result of sequentially activating each of the plurality of light emitting devices. The gain that is set for each given "optical channel" (e.g. each different detector output signal portion corresponding with a different emitter and the corresponding signal handling/conditioning/ processing applied to such portion) is also maintained for an associated dark time measurement for that optical channel. Such approach ensures that both the ambient light compensation and electronic offsets employed in detection componentry are computed for a selected optical channel at the same gain setting that is used to collect the input data generated for the selected optical channel. This individualized optical channel compensation combined with the common amplifier channel compensation and a fixed light source drive improves the accuracy of the resultant computations.

Numerous additional aspects and advantages of the present invention will become apparent upon consideration of the description that follows.

DETAILED DESCRIPTION

The typical medical monitoring instrument consists of two primary segments: an electronics/processor (control) module, resident within a monitor, and a probe that is attachable to a tissue site on a patient for performing the measurements of a desired physiological characteristic of the patient. Typically, the probe is interconnected to the monitor via a cable that delivers drive signals to light emitters comprising the probe or interconnected to the end of the cable for optical interface with the probe. Alternatively, the cable may deliver optical signals (e.g. via optic fiber(s)) from emitters in the monitor to the probe. The cable also delivers an output signal from a light detector(s) within the probe to the monitor for signal conditioning and processing.

Photoplethysmographic Probe Application

A pulse oximeter is a photoplethysmographic instrument that is typically used to monitor the condition of a patient in a hospital setting. The pulse oximeter instrument noninvasively, photoplethysmographically measures analytes present in the patient's arterial blood and produces a human readable display that indicates both the patient's heart rate and the oxygen saturation of the patient's arterial blood. These readings are important to enable the medical staff to determine whether the patient's respiratory system is functioning properly, e.g. supplying sufficient oxygen to the blood.

Pulse oximeters typically operate by utilizing a probe that transilluminates an appendage of the patient (such as a finger, ear lobe, or the nasal septum) that is rich in arterial blood and measures the amount of light that is absorbed by the pulsatile portion of the arterial blood to thereby determine oxygen saturation of the arterial blood. The pulse oximeter instrument often utilizes a plurality of light-emitting devices, each of which transmits light at a predetermined wavelength, which wavelengths are selected such that at least one is highly absorbed by oxygenated hemoglobin in the arterial blood and at least one is highly absorbed by reduced hemoglobin in the arterial blood. The amount of absorption of the light beams generated by these light emitting devices is a measure of the relative concentration of the oxygenated and reduced hemoglobin in the arterial blood. The absorption of the light that is being transmitted through the appendage of the patient includes a constant portion that is a result of skin, bone, steady-state (venous and non-pulsatile arterial) blood flow and light loss due to various other factors. The pulsatile component of absorption is due to the pulsatile arterial blood flow and is a small fraction of the received signal. The pulsatile component or both the pulsatile and non-pulsatile components may be used by the pulse oximeter instrument to perform its measurements.

The measurements are computed by periodically sampling the output of a light detector located in the probe. In time-division multiplexing applications, the samples are obtained in synchronization with sequential activation of the light emitting devices to determine the incremental change in absorption at the various wavelengths of light transmitted through the appendage of the patient. In frequency division multiplexing applications, the light emitting devices are modulated at different frequencies and the detector output is demodulated based upon such frequencies. Such demodulation allows the detector output signal samples to be employed to determine the change in absorption at the different centered wavelengths associated with the emitters. The incremental changes in light absorption are used to compute the oxygen saturation of the arterial blood as well as the patient's pulse rate. The pulsatile component of the signals received by the light detector represent only a small fraction of the incident light and it is important that the transmitted signals have sufficient amplitude and minimal noise to provide accurate readings.

Probe Signal Characteristics

In the field of medical monitoring instruments, it is essential to obtain sufficient signal output from the sensor devices that perform the measurements of the desired physiological characteristics of the subject to enable the monitoring instrument to compute an accurate result. The precise regulation of sensor operation is complicated by the fact that the sensor devices are typically located in a probe device, attached to the monitoring instrument at the end of a length of cable. This configuration and the hostile environment typically found in medical monitoring applications yields analog signals received at the monitoring instrument that are noisy and of small magnitude. It is therefore necessary to amplify the received analog signals to a level that is usable by the monitoring instrument without significantly distorting the received analog signals or introducing significant noise components.

System Architecture

Figure 1A:
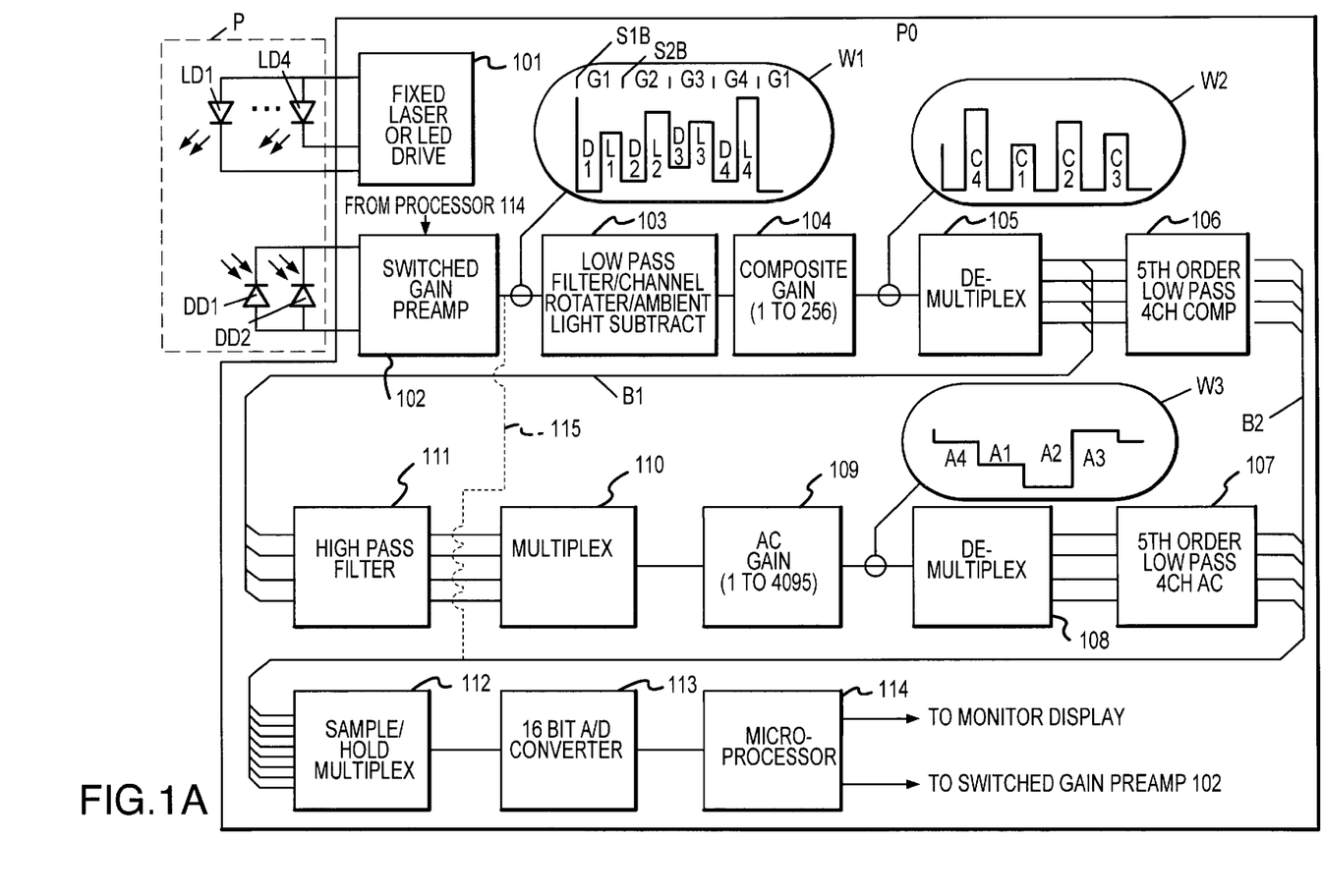
FIG. 1a illustrates one embodiment of the present invention in block diagram form, as implemented in a photoplethysmographic instrument

FIG. 1a illustrates in block diagram form the overall architecture of one embodiment of the present invention. In particular, a probe P affixable to a patient is attached via a cable to a monitoring instrument, such as a pulse oximeter P0. A fixed drive 101, which includes a drive control circuit operating in conjunction with a fixed light emitting device drive circuit, functions to provide a fixed drive to each of a plurality of light emitting devices LD1–LD4. By way of example, a different, fixed current drive signal may be provided to each of the light emitting devices LD1–LD4, wherein each of the devices LD1–LD4 produces a corresponding light beam of predetermined intensity at different selected center wavelengths. The emitting devices LD1–LD4, located in probe P, are individually and sequentially activated and cycled between an off state and an on state. The plurality of light emitting devices LD1–LD4 are therefore activated seriatim until all of the light emitting devices LD1–LD4 have been cycled off-on-off, and the cycle begins again for the next sampling interval.

At least one light detector DD1 is included in the probe P to measure the intensity of the light that emanates from the patient's appendage (e.g., a finger) and to output a multiplexed signal indicative thereof. The probe P of FIG. 1 illustrates the use of two light detectors DD1–DD2, to thereby more readily span the range of wavelengths produced by the light emitting devices LD1–LD4. The two light detectors DD1–DD2 are connected in parallel, and their output is connected via cable to a switched gain preamplifier 102 located in the pulse oximeter PO. As will be further described, in one arrangement switched gain preamplifier 102 may include a transimpedance amplifier and bootstrap amplifier interconnected across the detectors DD1–DD2 which eliminates the capacitance of the photodetector that comprises the light detectors DD1–DD2 and cabling as a factor in the response characteristics of the receiver circuit comprising the switched gain preamplifier 102. The gain of the receiver circuit can therefore be changed more rapidly. In turn, normalization of the plurality of optical channels can be more readily performed in the receiver circuit rather than in the light generation circuit comprising fixed drive 101.

The switched gain preamplifier 102 (as described in detail below) includes a gain stage and an application stage. The gain stage receives a digital input (e.g. from a microprocessor) to set the gain of the switched gain preamplifier 102. The digital signal is converted into a gain control signal by an analog switch circuit and applied in the amplification stage. The operation of fixed drive 101 and switched gain preamplifier 102 is time multiplexed in a synchronous fashion by a master clock and timing control circuit. Both a dark time and light output time corresponding with each light source are measured at the same preamplifier gain, thereby reducing error components in the resultant signals. That is, any error component that originates from the amplifier operation at a particular gain level is compensated for by making the dark time and light time measurements at the same amplifier gain. Similarly, and concurrently, the ambient light level is compensated for by measuring the ambient light (e.g., corresponding with a dark time) substantially concurrently with the light transmitted by the appendage from an activated light emitting device LD1–LD4. Thus, during each segment of a sampling cycle, both the present level of ambient light and the gain-specific error components are concurrently compensated.

Circuit Operation—Waveform Diagram

Waveform diagram W1 on FIG. 1a is illustrative of the operation of the switched gain preamplifier 102. The waveform is segmented into four sections, or signal portions, each of which is indicative of the response of the switched gain preamplifier 102 for a selected one of the four light emitting devices LD1–LD4. As noted above, the gain of the switched gain preamplifier 102 is set as a function of the particular light emitting device LD1–LD4 that is next in a predetermined sequential ordering for activation. Thus, for the first section of the waveform, the gain of the switched gain preamplifier 102 is set to a value of G1 at time S1B and maintained at this level until time S2B. The gain G1 is representative of the gain required for light emitting device LD1 during its on condition (L1) to maintain a signal output amplitude at the predetermined desired level. The gain G1 is also applied during the immediately precedent off time (D1) included within the first signal portion from time S1B to S2B, thereby enabling the pulse oximeter system to measure the signal level of the system during this dark time for the gain G1 used for the light emitting device LD1. Thus, the comparison of light "on" output to light "off" output is measured at the identical gain, which gain is selected specifically for the light emitting device LD1 that is presently being activated during this section of the waveform.

The signal levels present during the various gain time periods G1–G4 for the various dark times D1–D4 can vary significantly. If an average signal output for a dark time were to be used for all the output signals for the various light emitting devices LD1–LD4, a significant error component could be introduced into the resultant computations, since the signal during a dark time interval is a function of the system gain. The switched gain preamplifier 102 is set to a specific gain as a function of the characteristics of the presently active light emitting device, and since each on time has associated precedent dark time, the on time and precedent dark time measurements for each channel are made at the same gain to minimize the error in the subsequent computations.

Gain and Signal Determination

The amplified signals produced by switched gain preamplifier 102 are transmitted through low pass filter/channel rotater/ambient light subtraction circuit 103. The low pass filter/ambient light subtraction portions of circuit 103 correct the light measured by detectors DD1–DD2 by reducing the measured magnitude of the light detected as a result of activating a light emitting device LD1–LD4 by the amount of ambient light that is present. Thus, circuit 103 produces a signal that represents the difference between the signal magnitude during the $Dt_{1\ to\ 4}$ time period and the associated $Lt_{1\ to\ 4}$ time period. This signal difference represents the measured light intensity that emanates from the transilluminated appendage of the patient. Further, and as will be described below, the channel rotating portion of circuit 103 functions to rotate the timing sequence of the signal portions for periods G1–G4, which reduces the amount of switching noise introduced into the signals by the demultiplexing/multiplexing circuitry of circuit 103. The output signal produced by low pass filter/channel rotator/ambient light subtraction circuit 103 is amplified by composite gain circuit 104. The magnitude and sequence of the signal output by composite gain circuit 104 is illustrated in waveform diagram W2 in FIG. 1. As shown in waveform W2, signal portions C1–C4 corresponding with the emitter "on" portions L1–L4 of waveform W1 have been rotated in sequence (i.e. to yield a C4, C1, C2, C3 ordering). Further, the ambient light component of the signal portions have been removed.

Following the composite gain circuit 104 demultiplexer 105 separates the four time multiplexed optical channels corresponding with the D1/L1–D4/L4 signal portions of waveform W1 into four individual signal processing channels, wherein the signals for each of the optical channels are individually processed. The output of demultiplexer 105 is applied to bus B1 and concurrently to a 5th order low pass four channel compensation circuit 106.

The 5th order low pass four channel compensation circuit 106 filters out high frequency signal components and applies the resultant signals via bus B2 to four of the eight inputs of a sample and hold/multiplexer circuit 112. In another arrangement, circuit 112 may have 16 inputs, wherein the signals from circuit 106 are applied to 4 of the 16 inputs. The sample and hold/multiplexer circuit 112 stores the received signal values and sequentially outputs the stored signals to 16-bit analog to digital converter circuit 113 for conversion to a digital representation. The digitized signals from the four signal channels output by 5th order low pass four channel compensation circuit 106 represent the optical channel values and are used by processor 114 to set the gain of switched gain preamplifier circuit 102.

For example, processor 114 may set the gains for each optical channel via corresponding predetermined algorithms or reference values (e.g., stored in a look-up table) that have been established based upon known intensity output characteristics for the sources LD1–LD4 at their corresponding predetermined fixed drive current levels. As will be appreciated, circuit 106, bus B2, sample/hold multiplexer circuit 112 and A/D converter 113 combinatively provide a means for monitoring the amplitude of the output of detectors DD1–DD2, wherein processor 114 may provide appropriate digital signals to switched gain preamp 102 for selective gain setting on a channel-specific basis. Numerous other monitoring arrangements may be utilized. For example, the output from preamp 192 may be provided directly to bus B2 by an interconnect 115 for use in monitoring.

The four channels of signals output on bus B1 are also used to determine the light intensity received by the light detectors DD1–DD2. The high pass filter 111 removes undesired low frequency signal components and multiplexer 110 switches the filtered signals to common gain stage 109 where the AC component of the received signal (e.g., corresponding with the pulsatile component of the light detected by detectors DD1–DD2) is amplified by a predetermined amount to obtain the required signal magnitude. Waveform W3 illustrates the output signals A1–A4 that are produced for the four optical channels as a result of this gain operation. The amplified signals are demultiplexed by demultiplexer 108 for processing on an individual channel basis by 5th order low pass four channel compensation circuit 107. The resultant filtered signals are applied to another four channels of the sample and hold/multiplexer circuit 112. The sample and hold/multiplexer circuit 112 stores the received signal values and sequentially outputs the stored signals to 16-bit analog to digital converter circuit 113 for conversion to a digital representation. The digitized signals from the four signal channels output by 5th order low pass four channel compensation circuit 107 represent the optical channel measured light intensity values and are used by processor 114 along With the signals output by circuit 106 to determine the concentration of the desired analytes that are present in the arterial blood in a conventional manner.

As will be appreciated, a master clock may be employed with conventional timing control circuitry to synchronize operation of the various components of the described arrangement. For example, all components other than circuits 106, 107 and 111 may be synchronized in operation via a single master clock.

The described arrangement enables the use of a fixed drive 101 on the light emitting devices LD1–LD4. This is an important advantage, particularly when the light emitting devices LD1–LD4 are laser diodes since the gain of laser diodes cannot be readily and/or reliably adjusted over a wide range of intensity. Furthermore, if light emitting diodes are used for the light emitting devices LD1–LD4, then any significant change in the device drive can cause a shift in operating temperature and output wavelength, which causes errors in the computed measurements. Thus, the provision of a constant drive on the light emitting devices LD1–LD4, and the compensation for the resultant signal magnitude variations in the switched gain preamp 102 of the receiver circuit provide improved system performance. The use of switched gain for both the light and dark times also reduces the error component caused in prior systems by the use of a single dark time ambient measurement. Further, the use of a signal rotating scheme in the receiver circuit further reduces error components associated with demultiplexing/multiplexing switching.

Alternate System Block Diagram

Figure 1B:
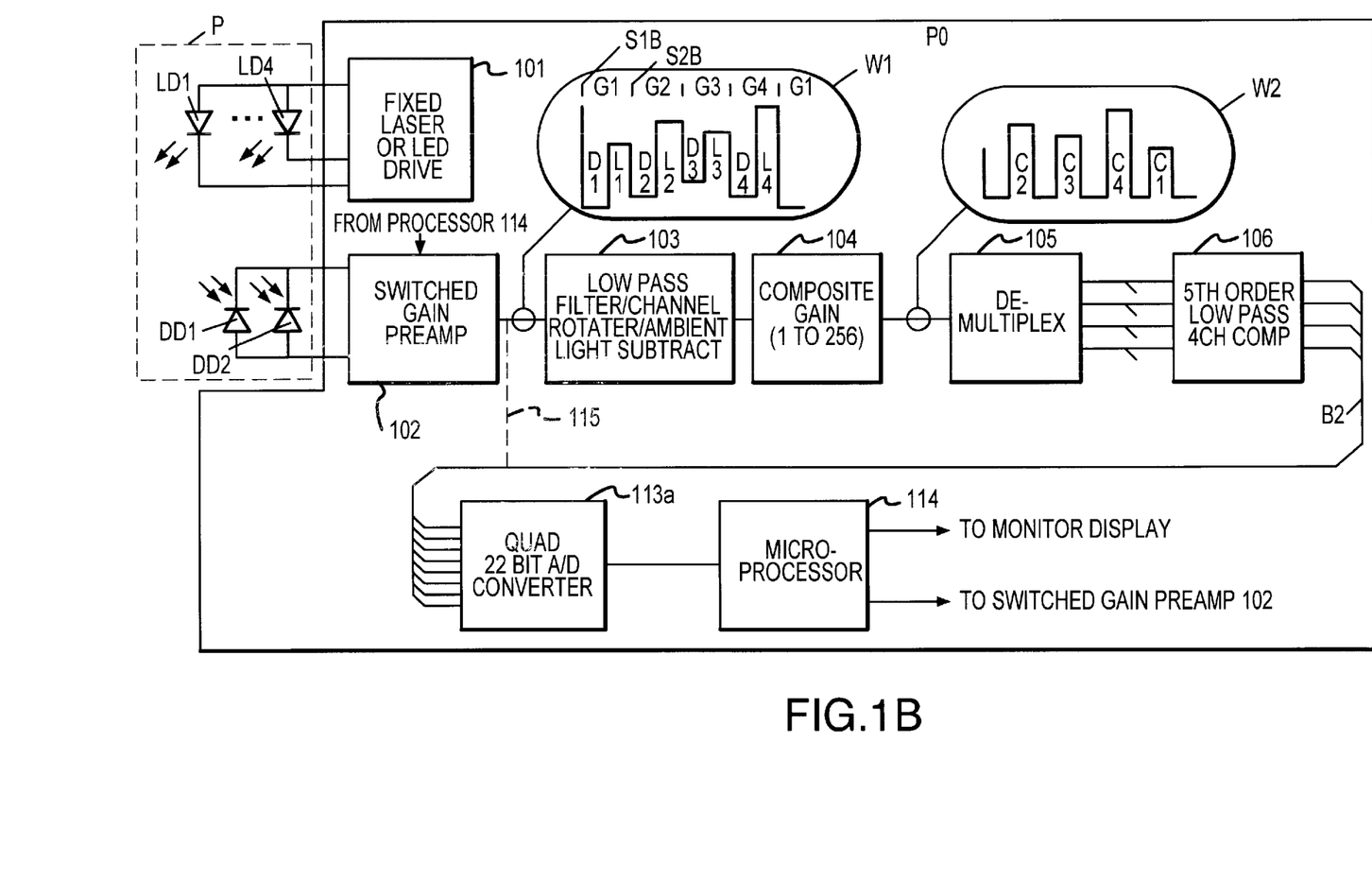
FIG. 1b illustrates the embodiment of FIG. 1a with modifications that eliminate the need for separating an AC component of a detection signal.

The embodiment depicted in FIG. 1b represents an improvement to the embodiment of FIG. 1a that is possible because of the use of high resolution analog to digital converters. With the use of analog to digital converters with greater than 20 bit resolution it may not be necessary to separate the AC component of the detection signal to obtain the resolution required to make accurate blood analyte calculations. This block diagram shows the outputs of the $5^{th}$ order low pass filters 106 being fed directly into a quad 22 bit analog to digital converter 113a, thus eliminating components 107 through 112 of the embodiment of FIG. 1a.

Switched Gain Transimpedance Bootstrap Amplifier Circuit Details

Figure 2:
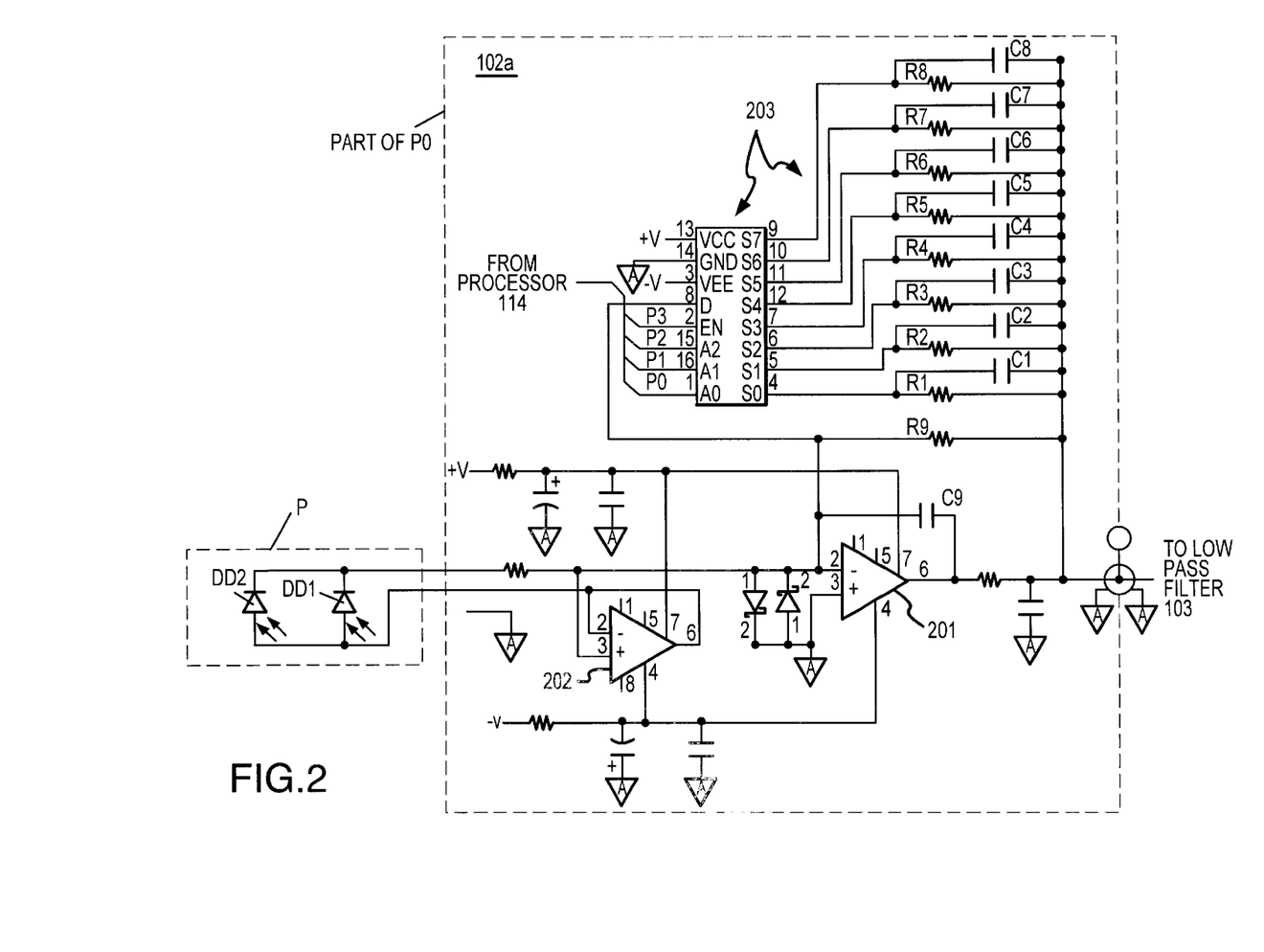
FIG. 2 illustrates details of one embodiment of a switched gain amplifier employable in the embodiments of FIGS. 1a and 1b.

The circuit details of one embodiment of the switched gain preamplifier 102 of the present invention are disclosed in FIG. 2.

In the illustrated switched preamp embodiment 102a, a transimpedance amplifier 201 (e.g., an inverting operational, or single stage differential, amplifier) functions as a current to voltage converter. An ideal current source has an infinite output impedance and produces an output current that is independent of the load that is presented to the current source. Photodetectors DD1–DD2 are basically current sources that have a finite but large output impedance. For small load impedances that are connected to photodetectors DD1 and/or DD2 the output impedance can be considered to be substantially infinite. The transimpedance amplifier 201 is interconnected at its inverting input to photodetectors DD1 and DD2, and presents an essentially zero impedance load to photodetectors DD1 and DD2 via the interconnection of the photodetectors DD1 and DD2 to the virtual ground of the summing junction of the transimpedance amplifier. Bootstrap amplifier 202 (e.g., a non-inverting unity gain, or non-inverting buffer, operational amplifier) provides a low impedance source to maintain substantially zero volts or bias across the photodiodes DD1 and DD2.

This bootstrap preamplifier configuration substantially eliminates the capacitance of the photodetectors DD1 and DD2 and cabling between the Probe P and pulse oximeter PO as a factor in the response characteristics of the transimpedance amplifier 201. The gain of the receive circuit can therefore be changed quite rapidly by the use of a switched gain determination circuit 203. As such, the normalization of two or more optical channels corresponding with two or more light sources can be performed more readily in the receiver circuit (e.g., rather than in the light generation circuit, thereby facilitating the use of fixed drive means).

A digital representation of the gain determined by the processor 114 is transmitted to the switched gain determination circuit 203. More particularly, the digital signal is provided to an analog multiplexer which connects one or more of a predetermined plurality of resistor-capacitor combinations (e.g., R1/C1–R8/C8) across a feedback network, which thereby sets the gain of the transimpedance amplifier 201.

Balanced Input Transimpedance Amplifier with Switched Gain

Figure 3A:
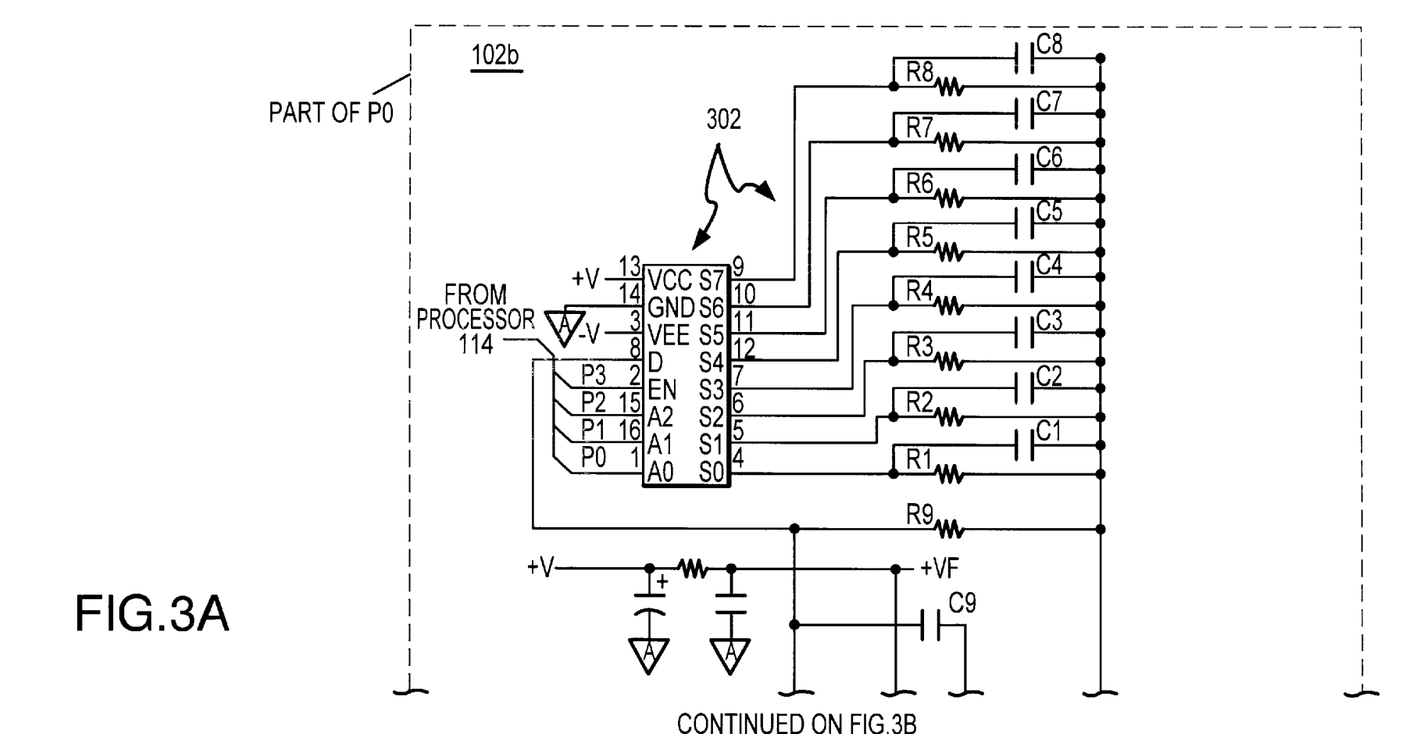
FIG. 3 illustrates details of another embodiment of a switched gain amplifier employable in the embodiments of FIGS. 1a and 1b.
Figure 3B:
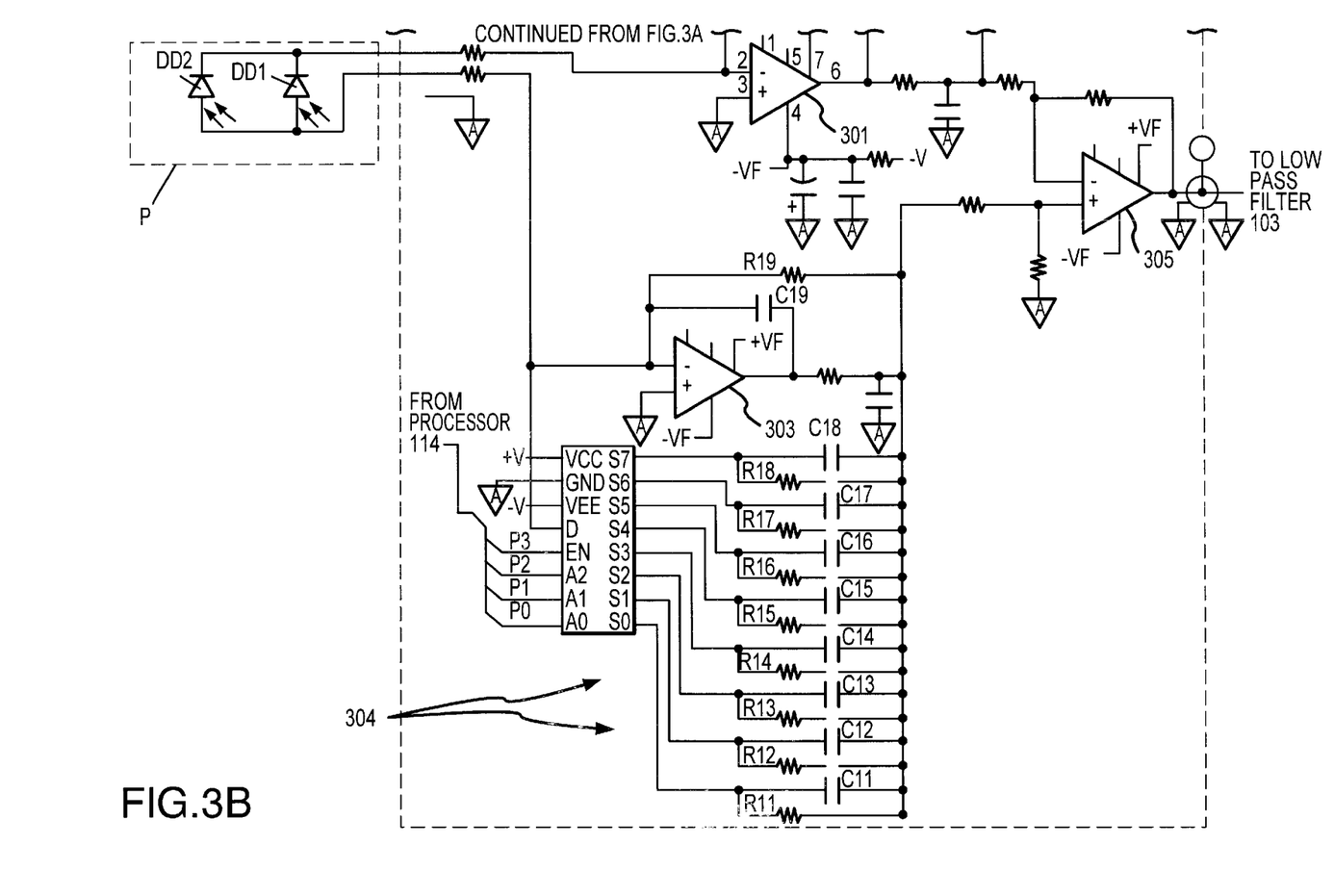

An alternate embodiment of a switched preamp 102b is disclosed in FIG. 3.

This circuit embodiment defines a balanced input transimpedance amplifier arrangement and is similar to the circuit of FIG. 2, except that the bootstrap amplifier in the FIG. 2 embodiment is replaced with a transimpedance amplifier 303 of opposite polarity to transimpedance amplifier 301. The gain applied to amplifier 303 is determined by a switched gain determination circuit 304 and is established to match the gain impedance determined by the switched gain determination circuit 302. The outputs of the transimpedance amplifiers 301 and 303 are summed by amplifier 305. This circuit provides a high common mode rejection to error signals coupled into the photodetectors DD1–DD2 or onto the cable connecting the photodetectors DD1–DD2 to the input of the transimpedance amplifiers 301 and 303 (e.g., error signals resulting from interference with electromagnetic emissions of other medical equipment, including e.g. electro-surgical pencils). This balanced input preamplifier configuration can be used with low capacitance photodiodes DD1 and DD2 and cabling to maintain high frequency response characteristics of the transimpedance amplifiers 301 and 303. In the illustrated arrangement, the digital representation of the gain determined by the processor 114 is transmitted to the switched gain preamp 102b at analog multiplexers in each of the switch gain determination circuits 302 and 304. Each of the multiplexers in switch gain determination circuits 302 and 304 connects one or more resistor-capacitor combinations (R1/C1–R8/C8 and R11/C11–R18/C18) across corresponding feedback networks which set the gains of the transimpedance amplifiers 301 and 303, respectively.

Alternate Balanced Input Transimpedance Amplifier with Switched Gain

Figure 4:
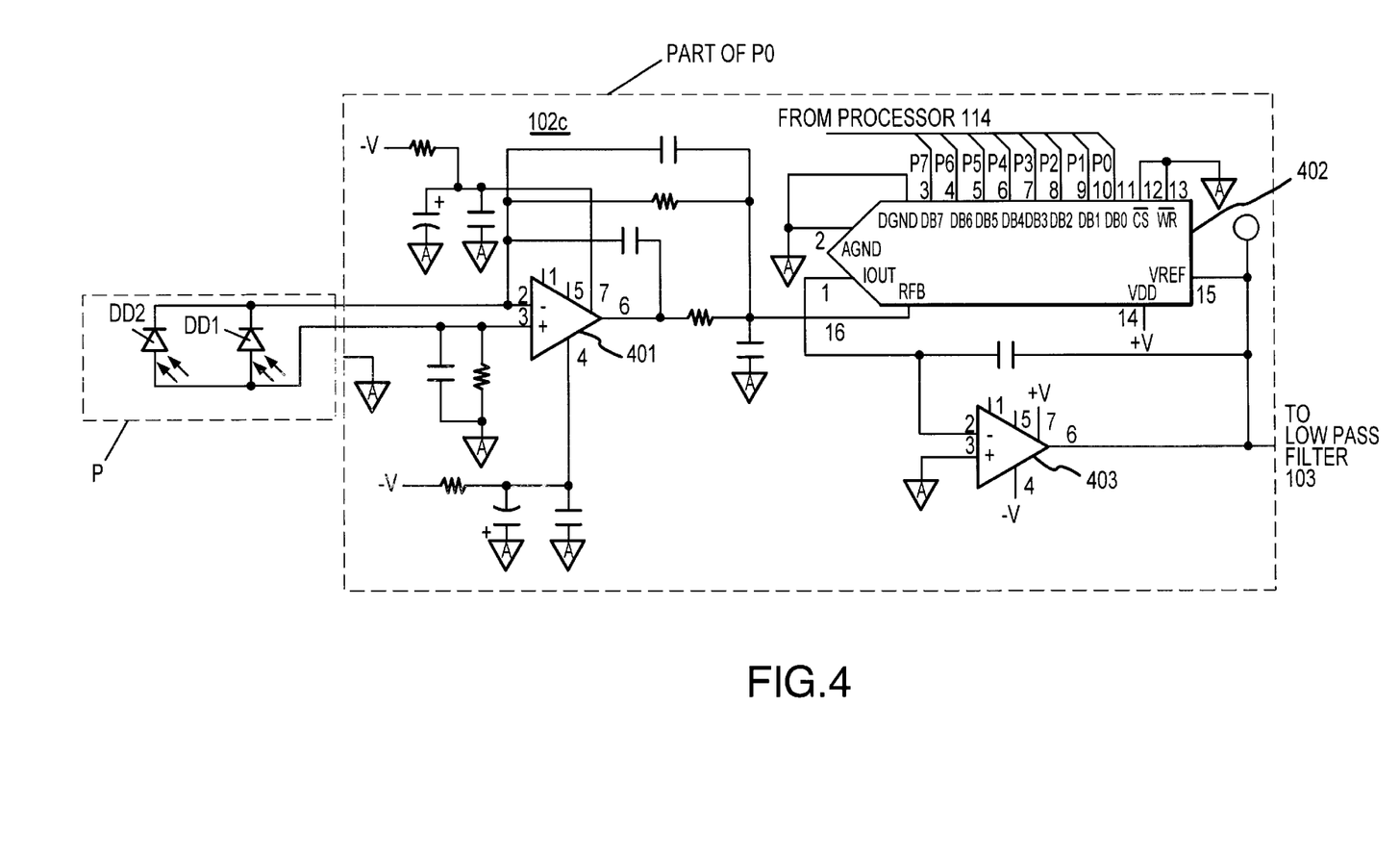
FIG. 4 illustrates details of yet another embodiment of a switched gain amplifier employable in the embodiments of FIGS. 1a and 1b.

Yet another embodiment of a switched gain amplifier 103c is disclosed in FIG. 4.

This circuit embodiment defines a balanced input transimpedance amplifier similar to the embodiment of FIG. 3, except that it has a single transimpedance amplifier 401 with a fixed gain and the switched gain is performed in a separate gain stage utilizing multiplex switch 402 and amplifier 403. This configuration uses fewer components and allows more flexibility in choosing the gain components 402 and 403.

Signal Channel Rotating Circuit

Figure 5:
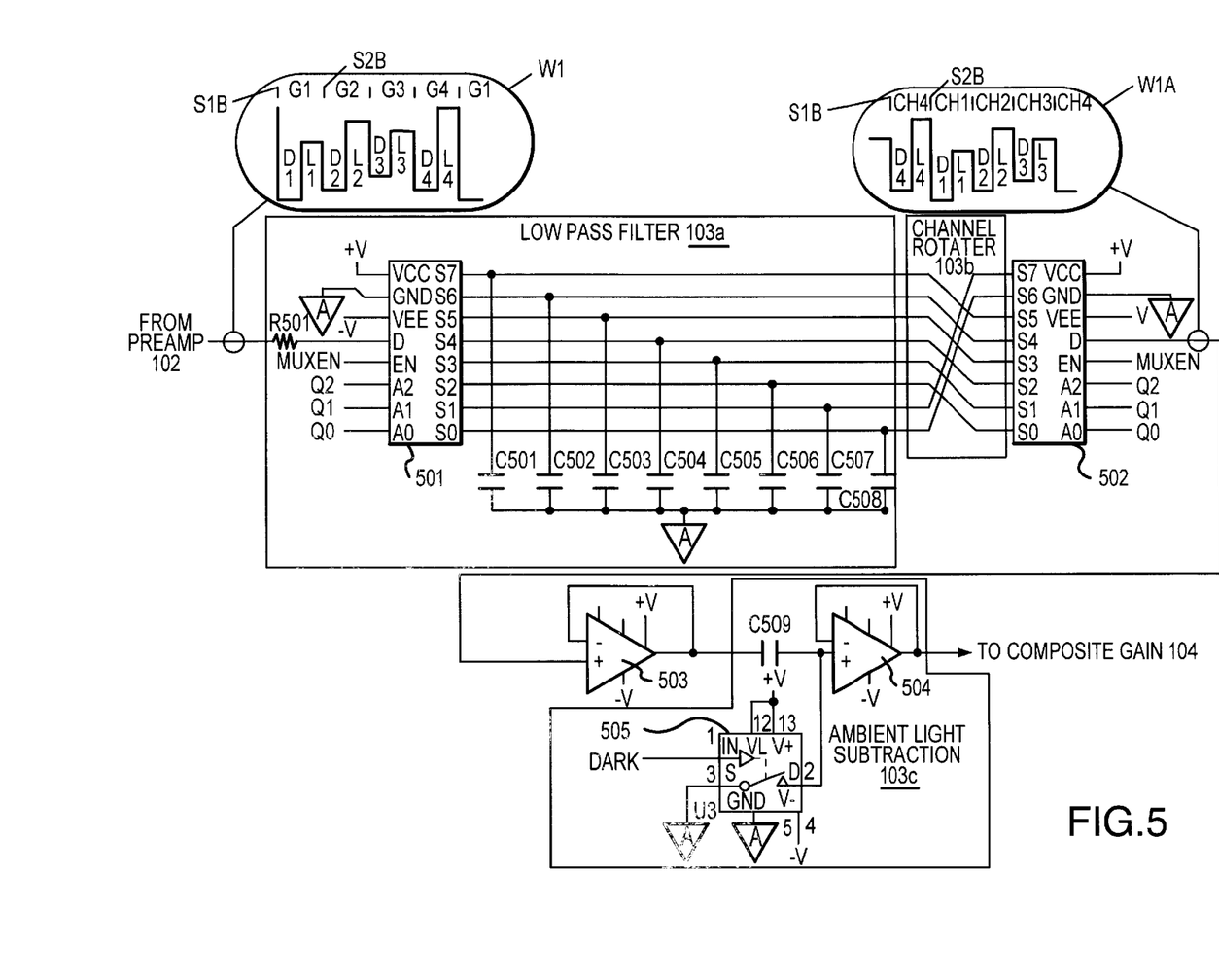
FIG. 5 illustrates details of an embodiment of the low pass filter/channel s rotator/ambient light subtraction circuit included in the embodiments of FIGS. 1a and 1b.

The circuit details of the low pass filter/channel rotator/ambient light subtraction circuit 103 are disclosed in FIG. 5.

The waveform WI represents the signal coming from the preamplifier circuit 102 as described under Circuit Operation—Waveform Diagram. In low pass filter portion 103a, each of the subportions of the waveform W1 (D1–D4 and L1–L4) undergoes demultiplexing onto separate channel lines by circuit element 501 and is low pass filtered by resistor R501 in conjunction with corresponding capacitors C501 through C508 (e.g., to yield 5 hertz filtering), with the intensity magnitude of each subportion being stored as a voltage on its respective channel line capacitor. In a channel rotator portion 103b, the voltages stored on the capacitors C501 through C508 are rotated as they are sent on their respective channel lines into the multiplexer circuit element 502. This remultiplexes the eight signals in a different order than they were coming into circuit element 501 as represented in waveform W1a. This channel rotator portion 103b allows the remultiplexing to avoid the switching noise created by the switching of signals onto the capacitors by circuit element 501. High impedance input buffer amplifier 503 reduces errors due to droop of the capacitors.

In ambient light subtraction portion 103C, ambient light and offset voltages from the preamp 102 are subtracted from the signal by capacitor C509 and the operation of circuit elements 504 and 505. Analog switch 505 is turned on during each dark time allowing capacitor C509 to charge up to the voltage present on the dark time capacitors C501, C503, C505, and C507 in seriatum. Then, the analog switch 505 is opened during each light time thus effectively subtracting each dark time voltage from the corresponding light time voltage. High impedance input buffer amplifier 504 then passes the multiplexed signal on to the composite gain stage.

The description provided above is not intended to limit the scope of the present invention. Numerous other arrangements and adaptations will be apparent to those skilled in the art.

I claim:

1. An apparatus for noninvasively measuring components of arterial blood in a patient, comprising:

a plurality of light emitting devices for emitting light of predetermined spectral content to illuminate a site on said patient that is perfused with arterial blood;

light detector means for receiving a portion of said light that is transmitted by the illuminated site;

amplifying means having a settable gain for separately amplifying a plurality of time-divided signal portions of a multiplexed detection signal indicative of said transmitted light received by the light detector means, wherein each of said plurality of time-divided signal portions includes a first subportion corresponding with activation of a corresponding one of said plurality of light emitting devices and a second subportion corresponding with a sequential dark time during which all of said plurality of light emitting devices are inactive.

2. The apparatus of claim 1, further comprising:

monitoring means for monitoring an amplitude of said multiplexed detection signal and for providing a control signal to set the gain of the amplifying means, wherein the amplitude of said multiplexed detection signal is maintained within a predetermined range.

3. The apparatus of claim 2, wherein:

said plurality of light emitting devices are sequentially activatable and deactivatable so that said multiplexed detection signal comprises a corresponding said plurality of time-divided signal portions; and said control signal is provided to separately set the gain of said amplifying means in relation to each of said plurality of time-divided signal portions.

4. The apparatus of claim 3, further comprising:

signal rotating means for receiving a first ordered signal corresponding with said multiplexed detection signal and for rotating a sequential order of said plurality of time-divided signal portions to provide a re-ordered signal.

5. The apparatus of claim 1, wherein said amplifying means comprises:

a first amplifier for maintaining a substantially zero bias across the detector means.

6. The apparatus of claim 5, wherein said first amplifier comprises:

a non-inverting operational amplifier having a first input interconnected to an input of said detector means and a second input interconnected to an output of said detector means.

7. The apparatus of claim 5, wherein said amplifier means further comprises:

a second amplifier for presenting a substantially zero impedance load to the detector means.

8. The apparatus of claim 7, wherein;

said detector means includes a photodiode;

said first amplifier includes a non-inverting operational amplifier having a first input interconnected to an input of said photodiode and a second input interconnected to an output of said photodiode; and said second amplifier includes an inverting operational amplifier having a first input interconnected to an output of said photodiode and a second input interconnected to a virtual ground and to said photodiode output.

9. The apparatus of claim 8, wherein said amplifying means further comprises:

a switching means for receiving said control signal and providing a predetermined gain signal to said second input of the inverting operational amplifier.

10. The apparatus of claim 2, further comprising:

a fixed drive means for providing fixed drive signals to sequentially activate each of said plurality of light emitting devices.

11. A method for noninvasively measuring components of arterial blood in a patient using a plurality of light emitting devices, each of which generates a beam of light of predetermined wavelength, to illuminate a site on said patient that is perfused with arterial blood, said method comprising the steps of:

applying fixed drive signals to activate said plurality of light emitting devices;

producing a multiplexed analog signal comprising a plurality of time-divided signal portions, using a light detector, indicative of an intensity of a portion of the light that is transmitted by said illuminated site, wherein each of said plurality of time-divided signal portions includes a first subportion corresponding with activation of a corresponding one of said plurality of light emitting devices and a second subportion corresponding with a sequential dark time during which all of said plurality of light emitting devices are inactive;

separately amplifying each of said plurality of time-divided signal portions of said multiplexed analog signal using an amplifier having a settable gain; and monitoring an amplitude corresponding with said amplified time-divided signal portions to provide a control signal to set the gain of said amplifier, wherein said monitoring an amplitude comprises subtracting said second subportion from said first subportion.

12. The method of claim 11, wherein said applying step includes sequentially activating each of said plurality of light emitting devices seriatim so that said multiplexed analog signal comprises a plurality of time-divided signal portions, and wherein the amplifying step comprises:

separately setting the gain of said amplifier in relation to each of said plurality of time-divided signal portions.

13. The method of claim 12, wherein each of said plurality of time-divided signal portions includes a first subportion corresponding with activation of a corresponding one of said plurality of light emitting devices and a second subportion corresponding with a sequential dark time during which all of said plurality of light emitting devices are inactive, and wherein said amplifying step includes maintaining said separately set gain the first and second subportions of each of the plurality of time-divided signal portions.

14. The method of claim 12, further comprising:

rotating a first ordering of said plurality of time-divided signal portions to provide a second ordering thereof.

15. The method of claim 11, wherein said amplifying step comprises:

maintaining a substantially zero bias across the light detector.

16. The method of claim 11 wherein said amplifying step further comprises:

presenting a substantially zero impedance to the light detector.

17. An apparatus for noninvasively measuring components of arterial blood in a patient, comprising:

a plurality of light-emitting devices for sequentially emitting light of a predetermined spectral content to illuminate a site on a patient that is perfused with arterial blood;

light detector means for receiving a portion of said light that is transmitted by the illuminated site; and signal rotating means for receiving a detection signal indicative of the light received by the detection means, wherein the detection signal comprises a plurality of portions each corresponding with a different one of the plurality of light sources, and wherein said rotating means rotates the order of the detection signal portions, in accordance with a predetermined ordering scheme to provide a reordered signal.

18. The apparatus of claim 17, further comprising:

demultiplexing means for providing each of said plurality of detector signal portions to said rotating means in corresponding separate channels; and multiplexing means for receiving each of a plurality of portions of said reordered signal from said rotating means and multiplexing said rotated signal portions.

19. The apparatus of claim 17, further comprising:

amplifying means having a settable gain for amplifying said detection signal.

20. An apparatus for noninvasively measuring components of arterial blood in a patient, comprising:

at least one light emitting device for emitting light of a predetermined spectral content to illuminate a site on said patient that is perfused with arterial blood;

a detector means for receiving a portion of said light that is transmitted by the illuminated site; and amplifying means for amplifying a detection signal indicative of said transmitted light received by the photodiode, and including a first amplifier for maintaining a substantially zero bias across the detector means.

21. The apparatus of claim 20, wherein said first amplifier comprises:

a non-inverting operational amplifier having a first input interconnected to an input of said detector means and a second input interconnected to an output of said detector means.

22. The apparatus of claim 21, wherein said amplifying means further includes a second amplifier for presenting a substantially zero impedance load to the detector means.

23. The apparatus of claim 22, wherein said second amplifier includes an inverting operational amplifier having a first input interconnected to an output of said photodiode and a second input interconnected to a virtual ground and to said photodiode output.

* * * * *

UNITED STATES PATENT AND TRADEMARK OFFICE
CERTIFICATE OF CORRECTION

PATENT NO. : 6,360,113 B1
DATED : March 19, 2002
INVENTOR(S) : Dettling

It is certified that error appears in the above-identified patent and that said Letters Patent is hereby corrected as shown below:

<u>Title page,</u>
Item [56], please insert
-- 4,603,700    8/1986     Nichols et al. ...... 128/633
   4,781,195   11/1988    Martin ................128/633
   4,800,885    1/1989     Johnson ..............128/633
   4,846,183    7/1989     Martin ................128/633
   5,782,758    7/1998     Ausec et al. ..........600/336
   5,954,644    9/1999     Dettling et al. ...... 600/322
   6,018,674    1/2000     Aronow ..............600/322
Jerald Graeme, "Circuit Options Boost Photodiode Bandwidth", 5/21/92 (p. 155-162), EDN-Design Feature --

<u>Column 10,</u>
Line 58, delete the "." and insert therefor --; and,
monitoring means for monitoring an amplitude corresponding with said amplified time-divided signal portions to provide a control signal to set the gain of the amplifying means, wherein said monitoring means substracts said second subportion from said first subportion for each of said amplified time-divided signal portions. --
Lines 59-64, after "1," delete "further comprising:
monitoring means for monitoring an amplitude of said multiplexed detection signal and for providing a control signal to set the gain of the amplifying means, wherein the amplitude of said multiplexed detection signal is maintained within a predetermined range.", and insert therefor -- , wherein: said monitoring means maintains the amplitude of said multiplexed detection signal within a predetermined range. --

Signed and Sealed this

Second Day of July, 2002

*Attest:*

JAMES E. ROGAN
*Attesting Officer*       *Director of the United States Patent and Trademark Office*